US008298822B2

(12) United States Patent
Kruse et al.

(10) Patent No.: US 8,298,822 B2
(45) Date of Patent: Oct. 30, 2012

(54) METHOD FOR THE PRODUCTION OF A CELL COMPOSITION CONTAINING EPITHELIAL CELLS

(75) Inventors: Charli Kruse, Herrnburg (DE); Gunter Fuhr, Berlin (DE); Thilo Wedel, Lubeck (DE)

(73) Assignee: Fraunhofer-Gesellschaft zur Förderung der Angewandten Forschung E.V., München (DE)

( * ) Notice: Subject to any disclaimer, the term of this patent is extended or adjusted under 35 U.S.C. 154(b) by 1303 days.

(21) Appl. No.: 11/547,678

(22) PCT Filed: Apr. 1, 2005

(86) PCT No.: PCT/EP2005/003430
§ 371 (c)(1),
(2), (4) Date: Dec. 31, 2007

(87) PCT Pub. No.: WO2005/097974
PCT Pub. Date: Oct. 20, 2005

(65) Prior Publication Data
US 2008/0193420 A1    Aug. 14, 2008

(30) Foreign Application Priority Data
Apr. 8, 2004 (DE) .......................... 10 2004 017 476

(51) Int. Cl.
C12N 5/00 (2006.01)
C12N 5/02 (2006.01)
C12N 5/071 (2010.01)
A01N 63/00 (2006.01)

(52) U.S. Cl. ........ 435/325; 435/371; 435/377; 424/93.7
(58) Field of Classification Search .......................... None
See application file for complete search history.

(56) References Cited

U.S. PATENT DOCUMENTS

| | | | | |
|---|---|---|---|---|
| 4,546,083 A * | 10/1985 | Meyers et al. | ................ | 435/400 |
| 5,122,470 A | 6/1992 | Banes | | |
| 5,190,878 A | 3/1993 | Wilhelm | | |
| 2003/0148510 A1 | 8/2003 | Mitrani | | |
| 2003/0165484 A1 | 9/2003 | Jianwu et al. | | |
| 2006/0194309 A1 * | 8/2006 | Fuhr et al. | ................. | 435/289.1 |

FOREIGN PATENT DOCUMENTS

| | | |
|---|---|---|
| DE | 197 25 602 | 1/1998 |
| DE | 19725602 A1 * | 1/1998 |
| DE | 198 01 763 | 7/1999 |
| DE | 102 23 536 | 12/2003 |
| EP | 12 60 580 | 11/2002 |
| EP | 13 04 370 | 4/2003 |
| WO | WO 95/11048 | 4/1995 |
| WO | WO 00/78929 | 12/2000 |
| WO | WO 0078929 A1 * | 12/2000 |
| WO | WO 01/68800 | 9/2001 |
| WO | WO 03/060055 | 7/2003 |
| WO | WO 2004074425 A2 * | 9/2004 |

OTHER PUBLICATIONS

Ramiya et al., Nature Medicine vol. 6, No. 3, Mar. 2000, pp. 278-282.*
Tokoro et al., Pancreatology vol. 3, No. 6, 2003, pp. 487-496.*
Bachem et al, Gastroenterol 115:421-432 (1998).
Grosfils et al.. Res Comm Chem Pathol Pharmacol 79:99-115 (1993).
Ramiya et al . "Reversal of Insulin-dependent Diabetes using Islets Generated In Vitro from Pancreatic Stem Cells". Nature Medicine, vol. 6, No. 3. Mar. 2000. pp. 278-282.
Tokoro et al , "Differentiation of Acinar Cells into Acinoductular Cells in Regenerating Rat Pancreas". Pancreatology, 2003. vol. 3. No. 6. pp. 487-496.
Kruse et al , "Pluripotency of Adult Stem Cells Derived from Human and Rat Pancreas", Appl Phys A Materials Science & Processing. 2004, vol. 79, No. 7, pp. 1617-1624.
Weissman et al , "Stem and Progenitor Cells: Origins, Phenotypes, Lineage Commitments, and Transdifferentiations". Annu Rev Cell Dev Biol., 2001, vol. 17. pp. 387-403.
Anderson et al , "The Human Plasma Proteome", Molecular & Cellular Proteomics. American Society for Biochemistry and Molecular Biology, Inc , 2002. vol. 1. No. 11. pp. 845-867.
Lakshmanan. J . "Nerve Growth Factor Levels in Mouse Serum: Variations Due to Stress". Neurochemical Research. 1987. vol. 12, No. 4, pp. 393-397.
Tai et al., "Role of Pancreatic Stem Cells in the Emergence of Pancreatic Stellate Cells and Fibro-blast-like Cells in Chronic Pancreatitis", Pancreas. Nov. 2003. vol. 27, No. 4, pp. 413-414.
Gao et al , "Characterization of Endocrine Progenitor Cells and Critical Factors for their Differentiation in Human Adult Pancreatic Cell Culture", Diabetes, Aug. 2003, vol. 52. No. 8. pp. 2007-2015.
International Search Report for PCT/EP2005/003430 mailed Mar. 22, 2006.

* cited by examiner

Primary Examiner — Chris R Tate
Assistant Examiner — Douglas F White
(74) Attorney, Agent, or Firm — Pearl Cohen Zedek Latzer, LLP (57) ABSTRACT

Disclosed is a method for forming epithelial cells. Said method comprises the steps of aggregating stem cells from differentiated exocrine gland tissue to obtain an organoid body and differentiating at least one portion of the organoid body or a tissue body grown therefrom to obtain epithelial cells. Also disclosed is a cultivation device, particularly for forming differential epithelial cells.

19 Claims, 5 Drawing Sheets

FIG. 11

METHOD FOR THE PRODUCTION OF A CELL COMPOSITION CONTAINING EPITHELIAL CELLS

PRIOR APPLICATION DATA

The present application is a National Phase Application of PCT International Application No. PCT/EP2005/003430, entitled "Method for the Production of a Cell Composition Containing Epithelial Cells", International Filing Date Apr. 1, 2005, published on Oct. 20, 2005 as International Publication Number WO 2005/097974, which in turn claims priority from German Patent Application Number DE 102004017476.8, filed Apr. 8, 2004, both of which are incorporated herein by reference in their entirety.

FIELD OF THE INVENTION

The invention relates to processes for producing epithelial cells, processes for cultivating epithelial cells, a cellular composition containing epithelial cells, a cultivation device for epithelial cells and uses of the cited cellular composition.

BACKGROUND OF THE INVENTION

Epithelial tissue is generally a tissue of epithelial cells that form cover layers on all outer and inner surfaces of multicellular organisms and on the one hand have mechanical protective and covering functions and on the other hand influence a substance exchange between the covered tissue and the environment. Epithelial tissue is multilayered as a rule in vertebrates and is built up, optionally from various types of epithelial cells. Outer epithelial cells are removed by mechanical wear or by dying off whereas epithelial cells are replicated from the inner tissue from a basal layer having dividing activity.

There is great interest in epithelial cells in biotechnology and medicine, especially in transplantation medicine, e.g., for encasing individual cells or cell cultures, covering tissue in an organism or filling in gaps in a tissue possibly produced by an injury or an operation. In so-called tissue engineering, in which cells of a certain origin are assembled to tissue with a certain function and/or form there is a particular interest in epithelial cells since they can assume in particular a carrier or matrix function in an artificially produced tissue of biological cells.

Problems result in the previous use of epithelial cells from the fact that the natural production in the organism usually is limited to the cited basal layer, that, however, is not available, e.g., in tissue engineering. Furthermore, rejection reactions after a transplantation may occur in an organism in the case of formation of a cell preparation with heterologous epithelial cells.

It is known that principally epithelial cells can also arise by differentiation from embryonic stem cells due to the pluripotent differentiation capability of embryonic stem cells. However, the generation of epithelial cells from embryonic stem cells is subject to limitations for ethical reasons and on account of the limited availability of embryonic stem cells and has not yet been satisfactorily effected in experiments of the past.

SUMMARY

The object of the invention is to provide an improved process for generating epithelial cells with which the disadvantages of the traditional processes are overcome and that in particular makes it possible to overcome the limitations associated with obtaining epithelial cells from basal layers or from embryonic stem cells. The invention's object is also to provide improved cellular compositions that can be produced with low cost and that have an expanded range of application. Another object of the invention is to provide a cultivation device for generating epithelial cells.

These objects are achieved by processes, cellular compositions and a cultivation device having the features as described herein. Advantageous embodiments and applications of the invention are also described herein.

As concerns the process, the above-cited embodiment is realized by an aggregation of stem cells isolated from differentiated exocrine gland tissue of an organism to three-dimensional cell aggregates and by a subsequent differentiation of at least a part of the cell aggregates to epithelial cells. The cell aggregates are also designated in the following as organoid bodies. A special advantage of this process resides in the complete decoupling of the generation of epithelial cells from the traditional use of basal layers or embryonic stem cells.

The inventors observed that the stem cells isolated from the exocrine gland tissue are pluripotent and exhibit a high ability to divide and a strong growth. Thus, they have a potential for providing starting materials for differentiating cells to epithelial cells on a large scale.

The exocrine gland tissue used in accordance with the invention can stem from an adult organism, a juvenile organism or non-human fetal organism, preferably from a postnatal organism. The concept "adult" as it is used in the present application thus refers to the development stage of the starting tissue and not to that of the donor organism from which the tissue stems. "Adult" stem cells are non-embryonic stem cells.

The exocrine gland tissue is preferably isolated from a salivary gland, lacrimal gland, sebaceous gland, sweat gland, from glands of the genital tract including the prostate, or from gastrointestinal tissue, including the pancreas, or from secretory tissue of the liver. A highly preferred embodiment concerns acinar tissue. The acinary tissue preferably stems from the pancreas, the parotid gland or the mandibular salivary gland.

A substantial advantage of the process of the invention is that the stem cells can be obtained from living donor organisms, e.g. from salivary glands without the donor organism being substantially adversely affected. This makes it possible to generate autologous epithelial cells with which the above-cited rejection reactions can be avoided upon transplantation into the donor organism.

In general, according to the invention the epithelial composition can be formed directly from the organoid body. However, according to a preferred embodiment of the invention a growth of the organoid bodies, e.g. in a suspension culture or an adhesion culture with supplying of nutrients, to larger bodies designated in the following as tissue bodies takes place at first. The inventors observed that the stem cells isolated from the exocrine glands form organoid bodies that exhibit a strong growth up to diameters of a few millimeters or more during the supplying of nutrients. The preparation of the epithelial cells from the tissue bodies has the advantage of a greater yield and effectiveness.

In general, the differentiation of the organoid body or of the tissue body can be initiated by adding a differentiation factor such as, e.g., a molecular growth factor or differentiated epithelial cells into the cultivation medium in order to generate epithelial cells and to optionally allow them to grow in the cultivation medium. However, according to a preferred variant of the invention the differentiation of cells of the organoid body to epithelial cells takes place by a cultivation on a boundary surface between a liquid and a gaseous medium. The inventors observed that the epithelial cells form spontaneously as soon as an organoid body or a tissue body extends out or grows out of the liquid cultivation medium into a gaseous environment, e.g., into the ambient air. In this case growth factors or stimulating cells in the cultivation medium can be dispensed with and the cultivation medium can be free of growth factors or stimulating cells. The organoid body exposed to the gaseous environment can consist of a few stem cells down to an individual cell.

It may be advantageous for a purposeful differentiation if according to another preferred embodiment of the invention the liquid surface of the liquid medium, e.g., of the cultivation medium, is shifted relative to the surface of the organoid body during the cultivation of the organoid bodies on the boundary surface between the liquid and gaseous media so that the organoid body increasingly projects out of the liquid medium in the course of the cultivation step.

This shifting of the liquid surface can be achieved in that at least one of the following procedures is provided simultaneously or successively. When the liquid surface is shifted due to the organoid body or the tissue body growing out of the cultivation medium, the differentiation rate is advantageously adapted to the growth rate of the organoid body. When the liquid surface of the liquid medium is lowered relative to the organoid body or the tissue body the differentiation rate can be advantageously influenced. When the liquid surface is lowered more rapidly that the tissue grows the differentiation rate can even be advantageously increased. The same applies in a corresponding manner for the lifting of a cultivation substrate with the organoid body out of the liquid medium.

The liquid surface is shifted with particular preference at a rate relative to the surface of the organoid body or tissue body that is adapted to a conversion rate during the differentiation of the aggregated cells of the organoid body or tissue body to epithelial cells. Since the cells inside the organoid body are mobile due to an inherent rearranging of the adhesive contacts to their particular surroundings, a rate of the liquid surface relative to the organoid body is preferably adjusted that is less than or equal to the rate of the cell movement in accordance with the molecular bonding rate of the cell contacts. In this manner the cells can adapt optimally to the differentiation conditions in the gaseous medium. The relative rate is, e.g., less than or equal to 1000 µm/h.

Particular advantages of the process of the invention can result if the differentiation procedure is directly linked with a shaping. In this manner certain tissue pieces can be produced whose form is adapted to the particular application, e.g., in transplantation tasks or tissue engineering. To this end, the differentiation of the organoid body or of the tissue body preferably takes place in the immediate vicinity of an imprint surface with a predetermined form that the differentiated epithelial cells follow.

Another embodiment of the invention provides for the massive formation of differentiated epithelial cells that the differentiated epithelial cells are separated from the organoid bodies or tissue bodies and are propagated separately. This propagation preferably takes place on a liquid-permeable cultivation substrate so that it is ensured that the epithelial cells are supplied with nutrients on all sides. A collagen fleece or a textile tissue is preferably used as cultivation substrate. These materials may be selected to be biocompatible and may remain a component of the epithelial cell composition even during its usage. According to preferred variants the propagation of the epithelial cells takes place on modified surfaces of the cultivation substrate such as, e.g., on surfaces containing fibrin or chitin.

If the propagation of the epithelial cells takes place on a deformable cultivation substrate, further advantages for the adaptation of the form of the epithelial cell composition to the desired application can result. Alternatively or additionally, the culture of the propagated epithelial cells may be subjected to a deformation, e.g., with a stamping or imprinting device.

The stem cells used for generating the epithelial cells are preferably isolated from an exocrine gland of a vertebrate, especially of a fish, a bird or a mammal, especially a human. In the case of the isolation of human stem cells the isolation takes place from juvenile or adult humans.

If the liquid surface of the cultivation medium is moved repeatedly, e.g., periodically or as an oscillation with a reversal of direction relative to the surface of the organoid body or of the tissue body during cultivation on the boundary surface and the organoid body or the tissue body is washed in a corresponding repeated manner with the cultivation medium or is exposed, this can result in advantages for an accelerated generation of the epithelial cells and their supply.

A cellular composition that contains at least one epithelial cell or consists completely of epithelial cells and is produced according to the process of the invention represents independent subject matter of the invention. Preferred applications of the cellular composition are present when used as drugs, in particular as an autologous drug, such as, e.g., as a transplant or part of a transplant, as material for tissue engineering applications. A preferred application of the epithelial cell composition of the invention consists in the synthetic preparation of biological tissue.

Concerning a device, the above-cited problem is solved by providing a cultivation device comprising a cultivation substrate for receiving at least one organoid body or tissue body in a cultivation vessel for receiving a liquid cultivation medium, a controlling means being provided for adjusting the liquid surface of the cultivation liquid in the cultivation vessel relative to the surface of the cultivation substrate. According to a first embodiment of the invention the controlling means comprises a placing means for positioning and/or shifting the cultivation substrate in a predetermined height in the cultivation vessel. Alternatively or additionally, the controlling means comprises a level control for adjusting a filling level of the cultivation liquid in the cultivation vessel.

According to a preferred embodiment of the invention the cultivation device of the invention is equipped with an imprinting tool that has an imprint surface for shaping the differentiated epithelial tissue.

BRIEF DESCRIPTION OF THE DRAWINGS

Further details and advantages of the invention are explained in the following with reference made to the attached drawings.

DETAILED DESCRIPTION OF THE INVENTION

Figure 1:
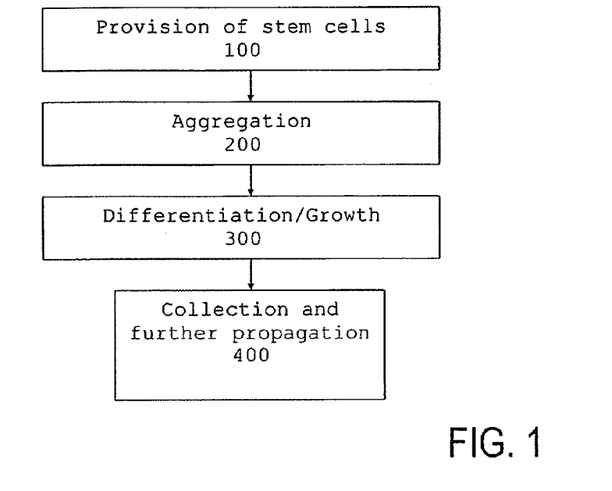
FIG. 1 shows a flowchart for illustrating an embodiment of the process in accordance with the invention.

In order to produce a composition of biological cells and/or tissue in accordance with the invention, according to FIG. 1, at first the stem cells isolated from a donor organism are provided (step 100), subsequently they aggregate to organoid bodies (step 200) that are subjected to a differentiation and/or to a growth (step 300) and finally to a collection and further processing, especially propagation (step 400). Although the steps 100 and 200 substantially comprise the aggregation step in accordance with the invention, whereas the steps 300 and 400 substantially represent the differentiation step in accordance with the invention and these two complexes are discussed separately in the following, it is stressed that partial steps of the differentiation may take place already within the framework of the aggregation and, vice versa, partial steps of the aggregation may be realized at first within the framework of the preparation. Thus, e.g., the differentiation of the organoid bodies may begin within the framework of the aggregation already or isolated stem cells can aggregate with organoid bodies that had already been pre-differentiated.

The embodiments of the invention explained in the following refer by way of example to the production of the biological material composition from stem cells removed from rats or humans. However, the implementation of the invention is not limited to these organisms but rather the corresponding processes can be realized with all organisms with differentiated exocrine glands with acinar tissue thus, e.g., with fish that have acinar tissue on the pancreas gland or mammals such as, e.g., cattle or sheep.

Figure 2:
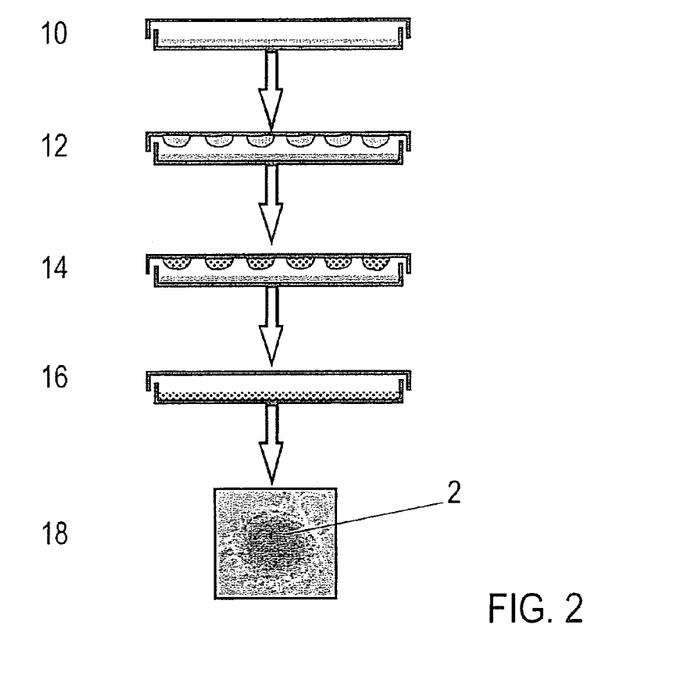
FIG. 2 shows an illustration of the formation of primary organoid bodies.

(I) Aggregation of Stem Cells from a Differentiated Exocrine Gland of a Living Organism to Organoid Bodies and/or Tissue Bodies According to the scheme shown in FIG. 2, in order to obtain the cells acinar tissue, preferably from a salivary gland or the salivary gland of the abdomen (pancreas), is received in culture in a mechanically and enzymatically comminuted form (step 10 in FIG. 2). Contrary to the indications of Bachem et al., Gastroenterol. 115:421-432 (1998) and Grosfils et al., Res. Comm. Chem. Path. Pharmacol. 79:99-115 (1993) no tissue blocks are cultivated from which cells are supposed to grow but rather the tissue is comminuted more strongly, with the proviso that the cell aggregations of the acini remain intact to the greatest extent possible.

These cells and cell aggregations are cultivated in culture vessels for several weeks. Every 2 to 3 days, the medium is changed, all differentiated cells being removed. The cells persisting in culture are non-differentiated cells with an unlimited capacity for division.

Similar cells have been isolated and described under the same conditions from the pancreas and designated as a type of myofibroblasts and pancreatic star cells (Bachem et al., 1998). However, in contrast to the cells of the present invention an unlimited ability to divide could not be observed. Furthermore, these cells were also not able to be passaged in an unlimited manner without loosing vitality.

In a second step (12) approximately 400 to 800 cells are cultivated in 20 µl medium in suspended drops. To this end the drops are placed on covers of bacteriological Petri dishes, turned upside down and placed over the Petri dish filled with medium so that the drops hang downward.

As a result of this type of cultivation cell aggregates (14) designated as organoid bodies form within 48 h and are transferred into a suspension culture for approximately 6 days (16). The partial view (18) in FIG. 2 shows a microscopic photograph of such an organoid body 2.

Figure 3:
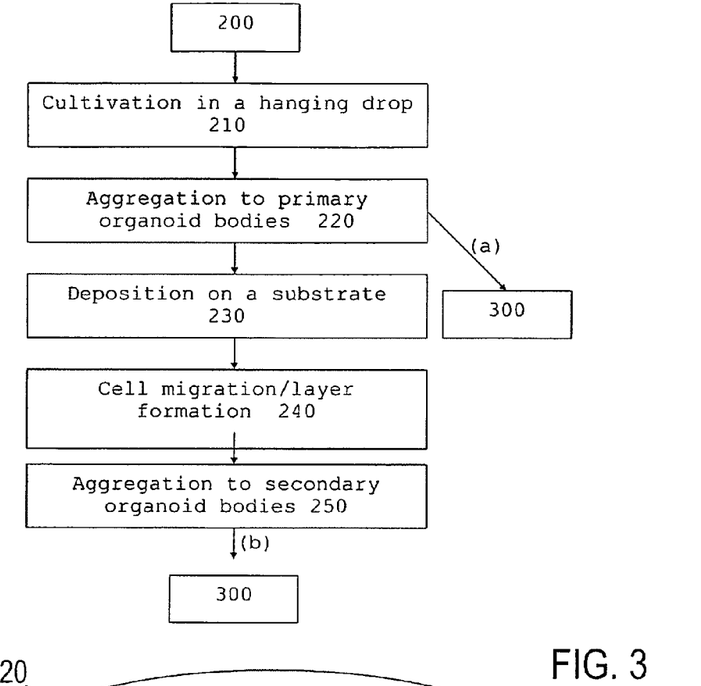
FIG. 3 shows a flowchart for illustrating further details of the process in accordance with the invention.

The various possibilities of providing organoid bodies as starting materials for further differentiation are compiled with further details in FIG. 3. The aggregation to the so-called primary organoid bodies (step 220) takes place after the above-described cultivation of the isolated stem cells in hanging drops (step 210), which primary organoid bodies can be subjected directly to the differentiation and the growth (step 300 in FIG. 1).

Figure 4:
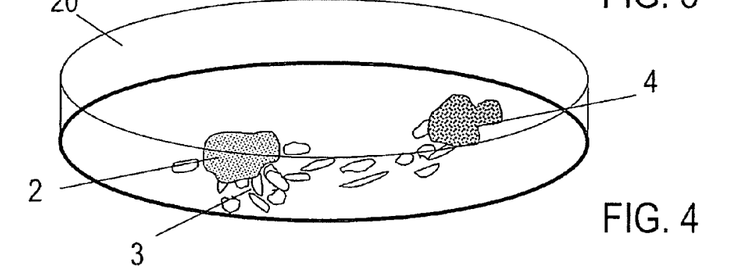
FIG. 4 shows the formation of secondary organoid bodies.

As an alternative, the depositing of the primary organoid bodies on a substrate (step 230) takes place at first for creating an adhesion culture (see FIG. 4 also). The inventors observed that the primary organoid bodies growing in suspension culture can form new organoid bodies in adhesion culture. The formation of a monolayer (step 240) on the substrate by cell migration follows and from this monolayer the aggregation to the so-called secondary organoid bodies follows (step 250). The latter can be subjected directly to the further differentiation and/or the growth (step 300).

The formation of the secondary organoid bodies is also illustrated in FIG. 4. Primary organoid bodies 2 first form a monolayer on the substrate of the adhesion culture such as e.g., on the bottom of culture dish 20 by a migration or growth of cells 3 from which monolayer then secondary organoid bodies 4 grow out. A further multiplication of the biomaterial is generated with the cultivation of primary organoid bodies 2 to secondary organoid bodies 4. Tissue bodies can grow from each of the primary or secondary organoid bodies 2, 4 during further cultivation.

Exemplary Embodiments for the Isolation and Aggregation of Stem Cells

The isolation and aggregation of stem cells is explained in detail in the following non-limiting examples.

The general working instructions customary for processes for cultivating biological cells and in particular mammalian cells are to be observed. A sterile environment in which the process is to be carried out is to be maintained in any case, even if no further description for this is given. The following buffers and media were used:

| | |
|---|---|
| HEPES stock solution (pH 7.6) | 2.383 g HEPES per 100 ml *A. bidest*. |
| HEPES Eagle's Medium (pH 7.4) | 90 ml modified Eagle's Medium (MEM) 10 ml HEPES stock solution |
| Isolation medium (pH 7.4) | 32 ml HEPES Eagle's Medium 8 ml 5% BSA in *A. bidest*. 300 µl 0.1 M $CaCl_2$ 100 µl Trasylol (200,000 KIU) |
| Digestion medium (pH 7.4) | 20 ml Isolation medium 4 ml collagenase (collagenase NB 8 from Serva) |
| Inkubation medium | Dulbecco's modified Eagle's Medium (DMEM) |
| Culture medium | Dulbecco's modified Eagle's Medium (DMEM) DMEM + 4500 mg/l glucose + L-glutamine – pyruvate + 20% FCS (inactivated) + 1 ml/100 ml pen/strep (10000 U/10000 µg/ml) or DMEM + 10% autoplasma + 1 ml/100 ml pen/strep, warm to 37° C. before use |
| Differentiation medium | 380 ml DMEM 95 ml 30 min at 54° C. inactivated FCS 5 ml glutamine (GIBCO BRL) 5 ml (3.5 µl β-mercaptoethanol per 5 ml PBS) 5 ml nonessential amino acids (GIBCO BRL) |

-continued 5 ml penicillin/streptomycin (GIBCO BRL)
(10000 U/10000 µg/ml)

Instead of fetal calf serum (FCS) in the culture medium and differentiation medium autoplasma, or, less preferably, autoserum of the tissue donor may also be used as an option. This is especially significant when the tissue donor is identical with the subsequent recipient of the stem cells or differentiated cells derived therefrom. Such an autologous treatment is preferred in order to prevent a possible rejection reaction.

Instead of the DMEM medium used, the culture medium may also contain another known basic medium suitable for the cultivation of eukaryotic cells, especially mammalian cells, as basic medium in which the differentiated cells die and the desired stem cells propagate. The isolation medium, incubation medium and differentiation medium may also contain another customary and suitable basic medium.

The following examples 1 and 2 describe in detail two working protocols for isolating and cultivating adult pluripotent stem cells from acinar tissue of the pancreas. Example 3 describes a corresponding protocol for the isolation from acinar tissue of the salivary gland.

EXAMPLE 1

1. Preparation of the Tissue and Isolation of the Cells

Using a syringe and a blunt cannula, 10 mL digestion medium was injected slowly and without bubbles into the pancreatic duct of two- to three-year-old rats. The entire pancreas is inflated by this procedure and thus, can be removed and prepared more easily. The pancreas is then transferred to a glass beaker and another 5 mL digestion medium is added. After removing the fatty tissue and lymph nodes, the tissue is divided very finely in the glass beaker using fine scissors, fatty tissue floating at the top is removed by suction and the suspension is then gassed with carbogen for one minute (repeating if necessary) and incubated for 20 minutes at 37° C., covered with aluminum foil, in an agitator at 200 cycles per minute. Then the medium is cautiously removed with suction, the tissue is divided again using scissors and the tissue fragments are washed twice each with 10 mL isolation medium and then 5 mL digestion medium is again added to the tissue.

After gassing with carbogen again for about one minute and incubating for 15 minutes at 37° C. in an agitator at 200 cycles per minute, the tissue fragments are divided by successively drawing out into a 10 mL, 5 mL, 2 mL and then a 1 mL glass pipette and pressed through a single layer of filter cloth. The cells isolated in this way are then washed five times in incubation medium (37° C.), gassed with carbogen and centrifuged for 5 minutes each time at 90 g. The pellet obtained finally is resuspended in incubation medium, gassed and distributed on tissue culture dishes.

2. Culturing the Cells

The tissue culture dishes with the isolated cells are cultured in an incubator at 37° C. and 5% $CO_2$. The medium is changed every 2 to 3 days, at which time all the differentiated cells are removed.

On the $7^{th}$ day in the culture, the cells are passaged using a solution consisting of 2 mL PBS, 1 mL trypsin and 2 mL incubation medium. In the course of this, the cells are detaching from the bottom of the culture dish. The cell suspension is centrifuged for five minutes, the supernatant is removed with suction and the cells are resuspended in 2 mL incubation medium, transferred to a medium-sized cell culture flask and 10 mL incubation medium is added. The medium is changed every three days.

On the $14^{th}$ day in culture, the cells are passaged again, but this time with 6 mL PBS, 3 mL trypsin and 6 mL incubation medium. The cell suspension is centrifuged for five minutes, the supernatant is removed with suction and the cells are resuspended in 6 mL incubation medium, transferred to three medium-sized cell culture flasks and 10 mL incubation medium is added to each.

The cells are cultured further and passaged and seeded until the cells achieve a semiconfluent to confluent state.

EXAMPLE 2

Pancreatic acini were obtained from male Sprague-Dawley rats (20 to 300 g) which had been anesthetized ($CO_2$) and exsanguinated through the dorsal aorta. A cannula was introduced transduodenally into the pancreatic duct and 10 mL digestion medium containing HEPES Eagle medium (pH 7.4), 0.1 mM HEPES buffer (pH 7.6), 70% (v/v) modified Eagle medium, 0.5% (v/v) Trasylol (Bayer AG, Leverkusen, Germany), 1% (w/v) bovine serum albumin, 2.4 mM $CaCl_2$ and collagenase (0.63 P/mg, Serva, Heidelberg, Germany) was injected into the pancreas posteriorly.

Before removing the pancreas it was partially freed of adhering fatty tissue, lymph nodes and blood vessels. Then healthy pancreatic tissue was placed in the digestion medium (at 20° C., lower metabolism), the pancreatic tissue was divided very finely with scissors, fatty tissue floating at the top was removed with suction and the tissue suspension was gassed with Carbogen (Messer, Krefeld, Germany) without allowing the nozzle to enter the medium with the cells (reducing mechanical stress) and the pH was adjusted to 7.4 in this way. Then the suspension was incubated at 37° C. in 10 mL digestion medium in a 25 mL Erlenmeyer flask (covered with aluminum foil) while agitating constantly (150 to 200 cycles per minute). After 15 to 20 minutes, the fat floating at the top and the medium were removed with suction and the tissue was divided again and rinsed with medium without collagenase (repeating the process at least twice, preferably until the cell fraction became transparent), whereupon digestion medium was added and the mixture was gassed again for about one minute with Carbogen. Digestion was again performed with collagenase for 15 minutes at 37° C. in an agitator using the same buffer. After digestion, the acini were dissociated by successively pulling up and ejecting through 10 mL, 5 mL and 2 mL glass pipettes with narrow openings and filtered through a single layer nylon mesh (Polymon PES-200/45, Angst & Pfister AG, Zurich, Switzerland) with a mesh of approximately 250 µm. The acini were centrifuged (at 37° C. and 600 to 800 rpm in a Beckman GPR centrifuge corresponding to approximately 90 g) and purified further by washing in incubation medium containing 24.5 mM HEPES (pH 7.5), 96 mM NaCl, 6 mM KCl, 1 mM $MgCl_{2,\ 2.5}$ mM $NaH_2PO_4$, 0, mM $CaCl_2$, 11.5 mM glucose, 5 mM sodium pyruvate, 5 mM sodium glutamate, 5 mM sodium fumarate, 1% (v/v) modified Eagle medium, 1% (w/v) bovine serum albumin, equilibrated with Carbogen and adjusted to a pH of 7.4. The washing procedure (centrifugation, suction removal, resuspension) was repeated five times. Unless otherwise indicated, the isolation procedure described above was performed at approximately 20° C.

The acini were resuspended in incubation medium and cultured at 37° C. in a humid atmosphere with 5% $CO_2$. The acinar tissue died rapidly under these conditions (within 2 days) and the dying differentiated cells separated from the adjacent cells without damaging the latter (gentle isolation) while the non-dying stem cells sank to the bottom and attached themselves. The differentiated acini cells are not capable of doing this. The incubation medium was changed for the first time on the second or third day after inoculating, with most of the freely floating acini and acinar cells being removed. At this point the first stem cells or their precursors had attached themselves to the bottom and had begun to divide. Then the medium was changed again every third day and differentiated acinar pancreatic cells were removed each time the medium was changed.

On the seventh day in culture the cells were passaged with a solution consisting of 2 mL PBS, 1 mL trypsin (+0.05% EDTA) and 2 mL incubation medium, whereupon the cells detached from the bottom of the culture dish. The cell suspension was centrifuged for five minutes at about 1000 rpm (Beckmann GPR centrifuge), the supernatant was removed with suction and the cells were resuspended in 2 mL incubation medium, transferred to a medium-sized cell culture flask and 10 mL incubation medium was added.

On the $14^{th}$ day in culture, the cells again were passaged, but this time with 6 mL PBS, 3 mL trypsin/EDTA and 6 mL incubation medium. The cell suspension was centrifuged for 5 minutes at 1000 rpm, the supernatant was removed with suction and the cells were resuspended in 6 mL incubation medium, transferred to three medium-sized cell culture flasks and 10 mL incubation medium was added to each.

On day 17 a third passage was performed on a total of six medium-sized cell culture flasks, and on day 24 a fourth passage was performed on a total of 12 medium-sized cell culture flasks. Now at the latest all the primary cells were removed from the cell culture except for the stem cells.

The stem cells may be cultured further, passages and inoculations being performed as frequently as desired. The inoculation is preferably performed in a density of $2\times10^5$ to $4\times10^5$ cells/cm$^2$ in incubation medium.

EXAMPLE 3

Isolation and culturing from exocrine tissue of the parotid gland of a human were performed by analogy with the pancreas protocol with the following deviations:
1. The exocrine tissue of the parotid gland was a mixture of acinar tissue and tubular tissue.
2. Since salivary glands contain less proteases and amylases than the pancreas, it is possible to store the salivary glandular tissue for a while under refrigeration at about 4° C. before workup without damaging the tissue too much. In the concrete example, the storage time was 15 hours and did not have any negative effects with regard to isolation of the desired stem cells.

Example 4 below describes in detail a working protocol for producing organoid bodies.

EXAMPLE 4

The undifferentiated cells are trypsinated with a solution of 10 mL PBS, 4 mL trypsin and 8 mL differentiation medium and then centrifuged off for five minutes. The resulting pellet is resuspended in differentiation medium so that a dilution of 3000 cells per 100 μL medium is established. Then the cells are suspended again well with a 3 mL pipette.

The cover is removed from bacteriological petri dishes that had previously been coated with 15 mL PBS (37° C.) per plate and the cover is inverted. Using an automatic pipette, approximately fifty 20 μL drops are placed on each cover. The cover is then turned over rapidly and placed on the petri dish filled with differentiation medium so that the drops hang down. The petri dishes are then cautiously placed in the incubator and incubated for 48 hours.

Next the aggregated cells in the hanging drops, forming the organoid bodies, are transferred from four covers each into one bacteriological petri dish with 5 mL incubation medium with 20% FCS and cultured for another 96 hours.

The organoid bodies are then cautiously collected with a pipette and transferred to cell culture vessels holding differentiation medium and coated with 0.1% gelatin. In an especially preferred embodiment of this method, 6 cm petri dishes coated with 0.1% gelatin are used as the culture vessels; 4 mL differentiation medium is placed in each in advance and then they are charged with six organoid bodies each. Another preferred culture vessel consists of chamber slides coated with 0.1% gelatin with 3 mL differentiation medium placed in each and then charged with three to eight organoid bodies each. In addition, 24-well microtiter plates coated with 0.1% gelatin with 1.5 mL differentiation medium placed in each well and then charged with four organoid bodies each may also be used.

When cultured in this way, the ability of the cells to differentiate into organoid bodies is activated and the cells can differentiate in particular into cells of the ectoderm. The cells may be stored and cultured both as organoid bodies or as individual cells and they retain their pluripotency.

(II) Differentiation in the Organoid Bodies and/or Tissue Bodies

The differentiation of cells in organoid bodies or tissue bodies can take place in general in a cultivation medium with an additive that influences the differentiation or on the boundary of a cultivation medium with a gaseous or vaporous environment. The following examples 5 and 6 describe working protocols for both variants.

EXAMPLE 5

For induction of differentiation, preferably stem cells after the $42^{nd}$ day of culturing were used. It is also possible to use stem cells after the third or fourth passage or cells stored for 12 to 18 months at the temperature of liquid nitrogen with no problem.

First the cells were transferred to differentiation medium having the composition given above and adjusted to a density of approximately $3\times10^4$ cells/mL, e.g., by trypsin treatment of a stem cell culture in culture medium, centrifugation for 5 minutes at 1000 rpm and resuspending the pellet in differentiation medium and diluting as much as necessary.

Then using a 20 μL pipette, approximately fifty 20 μL drops (600 cells/20 μL) were placed on the inside of the cover of a bacteriological petri dish (stoppered tip) and the covers were cautiously inverted over the petri dishes filled with PBS so that the drops would hang down. A new tip was used for each cover. The petri dishes were then cautiously placed in the incubator and incubated for 48 hours at 37° C.

Next the aggregated cells in the hanging drops, i.e., the organoid bodies, were transferred from four covers each into one bacteriological petri dish each with 5 mL incubation medium with 20% FCS (hold the cover obliquely and rinse off the organoid bodies with approximately 2.5 mL culture medium) and then cultured for five to nine more days, preferably 96 hours.

The organoid bodies were then collected cautiously using a pipette and transferred to cell culture vessels coated with 0.1% gelatin and containing differentiation medium. The organoid bodies would then proliferate and grow into partly isolated cell colonies which could then be further proliferated, isolated and proliferated again. In an especially preferred embodiment of this method, 6 cm petri dishes which were coated with 0.1% gelatin and into which 4 mL differentiation medium had already been placed were used as the culture vessels, each petri dish being charged with six organoid bodies. Another preferred culture vessel was chamber slides coated with 0.1% gelatin, into which 3 mL differentiation medium had been placed and which were then each charged with three to eight organoid bodies, and Thermanox plates (Nalge Nonc International, USA) for electron micrographic studies. Another alternative was 24-well microtiter plates coated with 0.1% gelatin with 1.5 mL differentiation medium placed in each well which was then charged with four organoid bodies each.

In a preferred embodiment of this method, organoid bodies were cultured for about 7 weeks in the gelatin-coated 6 cm petri dishes and then individual organoid bodies were cut out using the Microdissector (Eppendorf, Hamburg, Germany) according to the manufacturer's instructions and then transferred to fresh 6 cm petri dishes, chamber slides or Thermanox plates, for example.

EXAMPLE 6

Figure 5:
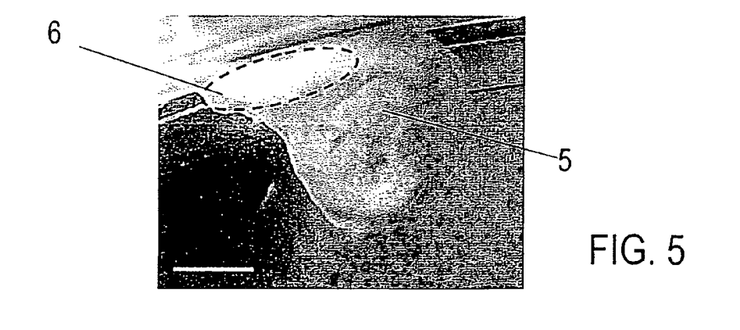
FIG. 5 shows a photograph of an organoid body.
Figure 6:
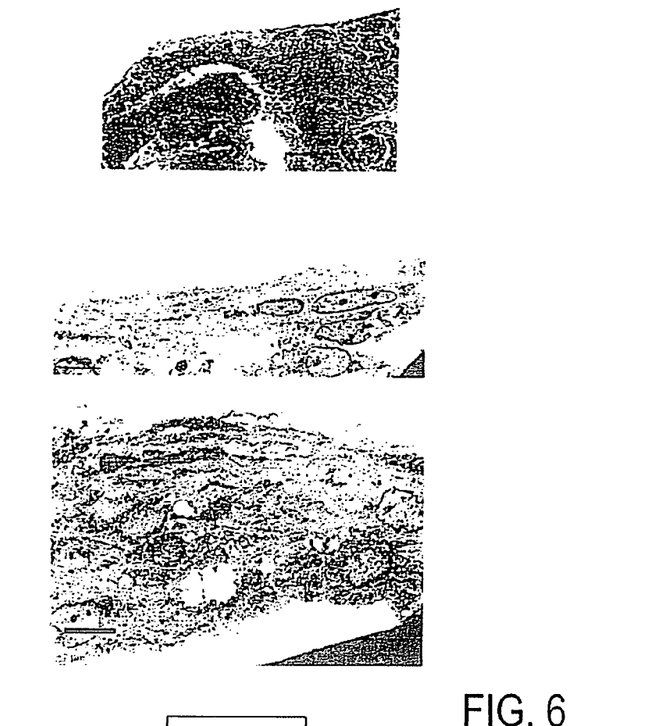
FIG. 6 shows optical and electron microscopic views of epithelial cells.

FIG. 5 shows by way of example a tissue body 5 growing in the adhesion culture (the white line corresponds to a length of 2 mm in the original), a part of the tissue body extending out of the cultivation medium. Tissue body 5 grew out of an organoid body formed in accordance with one of the processes indicated above. Epithelial cells 6 are generated in the part of tissue body 5 marked in dotted lines in the external air. Plate epithelia are produced up to a size of several millimeters. FIG. 6 illustrates light- and electronic microscopic views of differentiated epithelia (the black line in the lowest image corresponds to a length of around 7 μm in the original).

Figure 7:
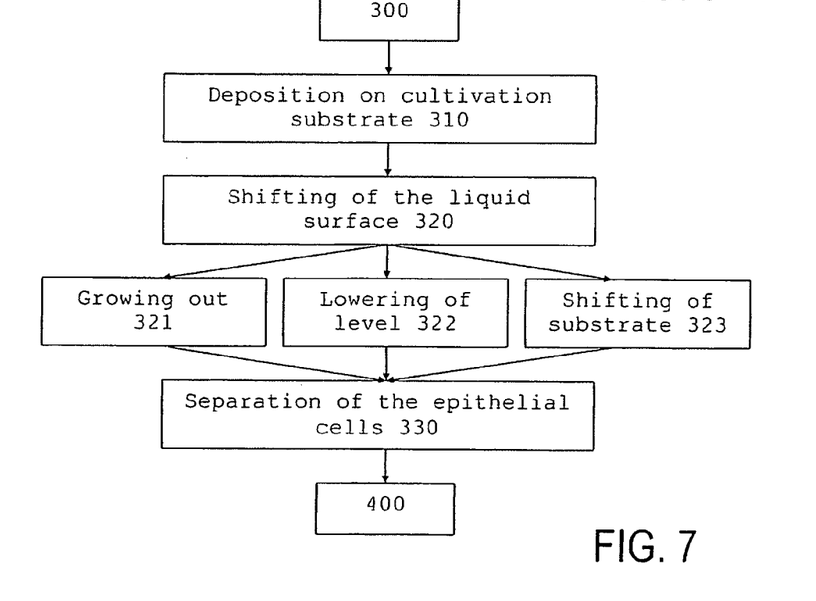
FIG. 7 shows a flowchart with further details of the process in accordance with the invention.

FIG. 7 illustrates further details of the process of the invention in the generation of epithelial cells on the liquid-solid border surface. The organoid bodies or tissue bodies produced in accordance with the process described above are deposited in step 310 on a cultivation substrate. The shifting of the liquid surface of the cultivation medium subsequently follows (step 320) until the top of the organoid body or tissue body touches the liquid surface. The further differentiation of the cells takes place in at least one of the three illustrated ways, namely, by growing out of the cultivation medium (step 321), by a lowering of the level of the cultivation medium (step 322) and/or by a shifting of the cultivation substrate (step 323). The epithelial cells generated are subsequently separated (step 330) and devoted to a further propagation (see step 400 in FIG. 1).

Figure 8:
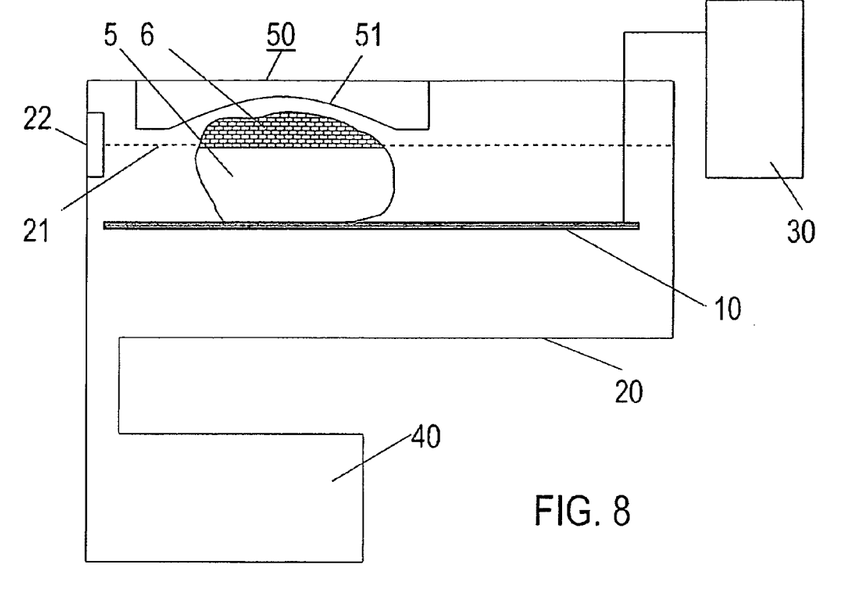
FIG. 8 shows a schematic diagram illustrating features of a cultivation device in accordance with the invention.

FIG. 8 schematically shows important components of a cultivation device in accordance with the invention with a cultivation substrate 10 that is arranged in such a manner that it can be shifted and fixed in certain positions in cultivation vessel 20. To this end positioning means 30 is provided as a controlling means with which cultivation substrate 10 can be positioned, e.g., with a piezoelectric actuator. Furthermore, filling level 21 of the cultivation liquid can be adjusted in cultivation vessel 20 with level control 40 comprising known fluidic components such as, e.g., valves and a pump. Sensor 22 is provided in order to monitor filling state 21 of the cultivation liquid in cultivation vessel 20. Sensor 22 is, e.g., an optical sensor or a conductivity sensor with which the filling level can be detected in a known manner. The sensor signal can be used to actuate positioning means 30 and/or level control 40 within the framework of a control circuit.

Imprinting tool 50 with imprint surface 51 with which a certain form can be impressed on the epithelial cells forming on the surface of tissue body 5 is located above liquid surface 21.

The operation of the cultivation device takes place in accordance with the scheme in FIG. 7 in such a manner that at first one or several tissue bodies 5 is/are deposited on cultivation substrate 10. A growing out of tissue body 5, a shifting of cultivation substrate 10 and/or an adjustment of filling level 21 until a part of tissue body 5 extends out of the cultivation medium and differentiates to epithelial cells subsequently take place.

The use of imprinting tool 50 in accordance with FIG. 8 is not obligatorily necessary. The shaping of the epithelial tissue can take place subsequently in the further propagation of the differentiated epithelial cells (step 400, see FIG. 1). Typical process steps of the further propagation are compiled in FIG. 9.

Figure 9:
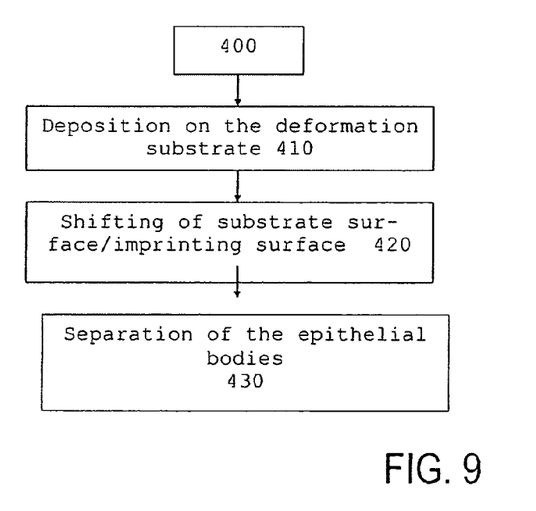
FIG. 9 shows a flowchart with further details of the process in accordance with the invention.

The deposition of the differentiated epithelial cells on a deformation substrate (step 410) takes place at first. The shifting of the substrate surface (step 420) subsequently takes place so that the epithelial cells form a desired shape. This shifting may be combined with an additional shaping with an imprinting tool. Finally, the separation of the epithelial body (step 430) takes place.

The deformation substrate, whose details are described with reference made to FIGS. 10 and 11, serves for the reception and the growth of epithelial cells as well as their shaping. It may have a deformable surface itself and/or function as carrier of the epithelial cells during the action of a imprinting tool.

Figure 10:
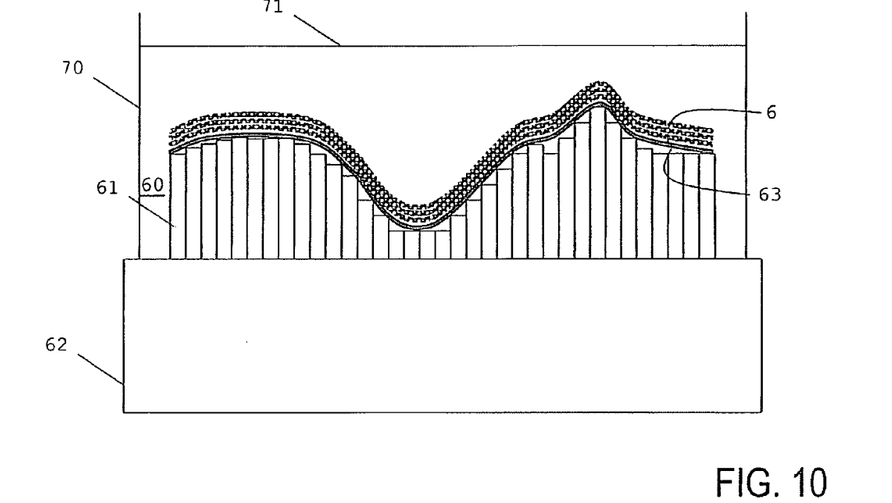
FIGS. 10 and 11 show schematic illustrations of devices for tissue engineering.

FIG. 10 illustrates a deformation substrate 60 including a plurality of forming elements 61 that can be shifted individually with positioning means 62 attached to a base part (not shown). Each forming element 61 has an ashlar form with a top. The total number of tops or at least one flexible, layered cover element 63 arranged on the latter form the surface of deformation substrate 60 used for the shaping on epithelial composition 6. The tops of forming elements 61 have typical dimensions in a range of 0.01 mm to 5 mm. Forming elements 61 are aligned in such a manner that the tops form a matrix arrangement consisting of straight rows and columns. The shifting of forming elements 61 relative to the base part takes place, e.g., with servomotors or piezoelectric drives. The surface is structured in accordance with the selected advance of a forming element 61.

Covering element 63 has the advantages that the tool surface is locally smoothed and the removal of cell material 6 from the tool is facilitated. Covering element 63 comprises, e.g., a foil (e.g., polyurethane) or a membrane that extends over all forming elements 61 and on which the cells are arranged. Alternatively, one or more covering elements can be provided that extend only over one or several partial groups of forming elements. A detachable adhering of covering element 63 to some or all tops of forming elements 61 can be provided.

Covering element 63 may consist of a synthetic polymer material and/or of a material naturally occurring in biological organisms such as, e.g., chitin or bone matrix material in one or more layers. Furthermore covering element 63 may bear a structured coating that on the one hand promotes an adherent adhesion of biological cells in partial areas and on the other hand blocks it in other partial areas.

In order to shape epithelial material 6 it is first arranged on the surface of deformation substrate 60, that is, the totality of the tops or the common covering element 63. To this end, e.g., a deposit of a plurality of organoid bodies or tissue bodies is provided in cultivation medium 71 in culture vessel 70. Subsequently, a growth of the organoid bodies or tissue bodies and a shifting of the surface of deformation substrate 60 by advancing forming elements 61 into the particular desired positions take place. This advance takes place at the above-indicated molecular bonding rate of the cells so that the cells can be displaced and rearranged without injury during the deformation of the cell material. A separation of the cell material as epithelial bodies from deformation substrate 60 can subsequently take place.

Figure 11:
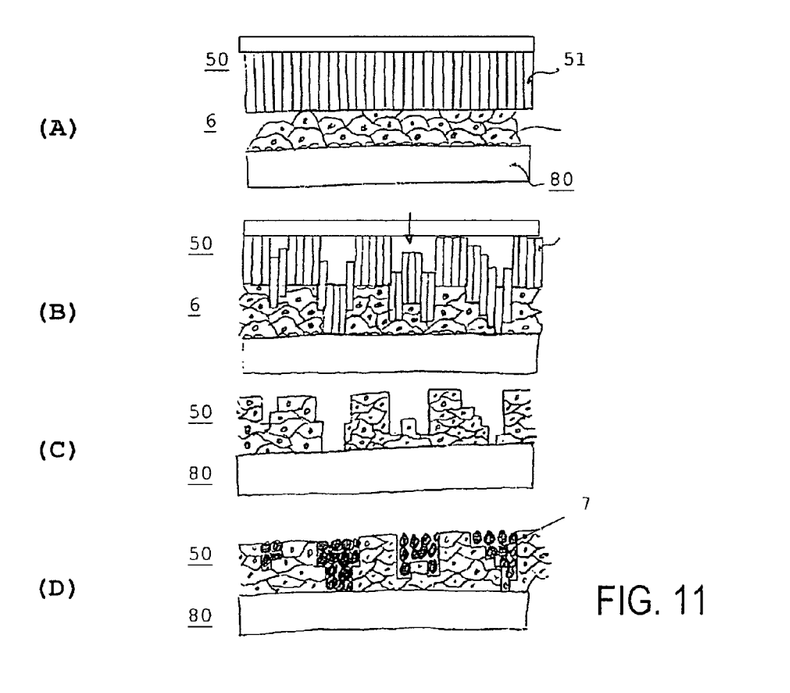

A deformation substrate according to FIG. 10 may alternatively be used as imprinting tool 50, as is illustrated in the image sequence according to FIG. 11. Epithelial cell material 6 to be deformed is present in an initial situation according to partial image A on a support 80. The imprinting tool 50 with the plurality of shiftable forming elements 51 is arranged above the surface of the cell material 6 that is free at first. The imprinting tool 50 is approached to the cell material 6 until the tops, that face downward in this instance, make contact with the cell material 6. Subsequently, an adjustment of the imprinting surface of the imprinting tool 50 takes place according to partial image B by the purposeful advance of individual forming elements 51. The advancing movement takes place at the above-indicated molecular bonding rate of biological cells. The individual forming elements 51 displace the cells in the cell material without injury.

Subsequently, the imprinting tool 50 is removed according to partial image C. The surface form of the tool remains as a complementary structure in the cell material 6. In order to facilitate the separation of the imprinting tool 50 from the cell material 6 the tops of the forming elements 51 can be provided with a coating to which an adherence of cells is prevented. The coating takes place, e.g., with the polymer poly-HEMA. Finally, the gaps imprinted in the cell material can be filled according to partial image D with other cells 7 or a synthetic matrix material.

The selection of the form and optionally of cells or additives 7 introduced into the cell material takes place in accordance with the concrete task within the framework of tissue engineering. For example, epithelial cells with a predetermined structure can be brought into a combination with tissue cells with a sequence according to FIG. 11.

The features of the invention disclosed in the above description, the claims and the drawings can be significant individually as well as in combination for the realization of the invention in its various embodiments.

The invention claimed is:

1. A process for the generation of epithelial cells, comprising:
    aggregating stem cells from differentiated exocrine glandular tissue to an organoid body, and
    differentiating at least a part of the organoid body or of a tissue body grown therefrom to epithelial cells, wherein the differentiation comprises a cultivation of the organoid body or the tissue body on a boundary surface between liquid and gaseous media wherein at least one cell of the organoid body or the tissue body extends out of the liquid cultivation medium into the gaseous medium, wherein either
    i) a liquid surface of the cultivation medium is not shifted relative to the surface of the organoid body or tissue body during the cultivation on the boundary surface; or
    ii) a liquid surface of the cultivation medium is shifted relative to the surface of the organoid body or tissue body during the cultivation on the boundary surface and wherein the shifting of the liquid surface takes place at a rate relative to the surface of the organoid body or of the tissue body that is adapted to a conversion rate for differentiating cells of the organoid body or of the tissue body to epithelial cells.

2. The process according to claim 1, wherein the shifting of the liquid surface comprises simultaneously or successively one or more of the following steps:
    growing out of the organoid body or of the tissue body from the cultivation medium,
    lowering of the liquid surface of the cultivation medium, and
    raising of a cultivation substrate with the organoid body or the tissue body from the cultivation medium.

3. The process according to claim 1, wherein the process is the process of alternative step ii.

4. The process according to claim 1, wherein the shifting of the liquid surface takes place at a rate relative to the surface of the organoid body or of the tissue body that is less than or equal to a molecular bonding rate of the cells of the organoid body or of the tissue body.

5. The process according to claim 3 or 4, wherein the rate is less than or equal to 1000 µm/h.

6. The process according to claim 1, wherein the differentiation of the organoid body or of the tissue body takes place in the immediate vicinity of an imprinting surface in such a manner that a geometric arrangement corresponding to the form of the imprinting surface is imprinted on the epithelial cells.

7. The process according to claim 1, wherein the aggregating comprises an association of stem cells isolated primarily from the exocrine tissue to primary organoid bodies or comprises an association of stem cells derived from the primary organoid bodies to secondary organoid bodies.

8. The process according to claim 1, wherein the differentiated epithelial cells are separated from the organoid body or from the tissue body and propagated.

9. The process according to claim 8, wherein the propagation takes place on a liquid-permeable cultivation substrate.

10. The process according to claim 9, wherein the propagation takes place on a collagen fleece or a textile tissue.

11. The process according to claim 8, wherein the propagation takes place on a fibrin-containing surface.

12. The process according to claim 8, wherein the propagation takes place on a chitin-containing surface.

13. The process according to claim 1, wherein the propagation of the epithelial cells takes place on a deformable cultivation substrate.

14. The process according to claim 8, wherein the culture of the propagated epithelial cells is subjected to a deformation with an imprinting tool.

15. The process according claim 8, wherein the stem cells are isolated from a gland of a vertebrate.

16. The process according to claim 15, wherein the stem cells are isolated from a gland of a fish, a bird or a mammal.

17. The process according to claim 16, wherein the stem cells are isolated from a juvenile or adult human.

18. The process according to claim 1, wherein during the cultivation on the boundary surface the liquid surface, of the cultivation medium is repeatedly shifted with a reversal of direction relative to the surface of the organoid body or of the tissue body so that the organoid body or the tissue body is repeatedly submerged in and reappears from the cultivation medium.

19. The process according to claim 18, wherein a periodic movement of the liquid surface of the cultivation medium relative to the surface of the organoid body or of the tissue body is provided.

* * * * *